United States Patent [19]

Kato

[11] 4,420,339
[45] * Dec. 13, 1983

[54] COLLAGEN FIBERS FOR USE IN MEDICAL TREATMENTS

[75] Inventor: Tadaaki Kato, Tokyo, Japan

[73] Assignee: Kureha Kagaku Kogyo Kabushiki Kaisha, Nihonbashi, Japan

[*] Notice: The portion of the term of this patent subsequent to Jun. 16, 1998 has been disclaimed.

[21] Appl. No.: 359,309

[22] Filed: Mar. 18, 1982

[30] Foreign Application Priority Data

Mar. 27, 1981 [JP] Japan ................................ 56-46021
Mar. 27, 1981 [JP] Japan ................................ 56-46022

[51] Int. Cl.³ .................... C07G 7/00; C08L 89/06
[52] U.S. Cl. .................................... 106/124; 106/155; 106/161; 260/123.7; 260/117; 424/177; 204/158 S
[58] Field of Search ................ 260/112 B, 123.7; 106/124, 155, 161; 424/177; 204/158 S

[56] References Cited

U.S. PATENT DOCUMENTS 3,867,269  2/1975  Shimonishi ..................... 204/158 S
4,273,705  6/1981  Kato .................................. 260/123.7

OTHER PUBLICATIONS

Chem. Abst. 74:88,693q 1971, Schaller et al.

Primary Examiner—Theodore Morris
Attorney, Agent, or Firm—Wegner & Bretschneider

[57] ABSTRACT

Disclosed herein are collagen fibers for use in medical treatments, having amino acid residues of 312 to 340 glycine residues, 119 to 138 proline residues, 94 to 100 hydroxyproline residues and 2.6 to 5.5 tyrosin residues per 1000 total amino acid residues thereof, a denaturation temperature in a range of 31° to 40° C., and S-constant of 1.12 to 1.62.

6 Claims, 1 Drawing Figure

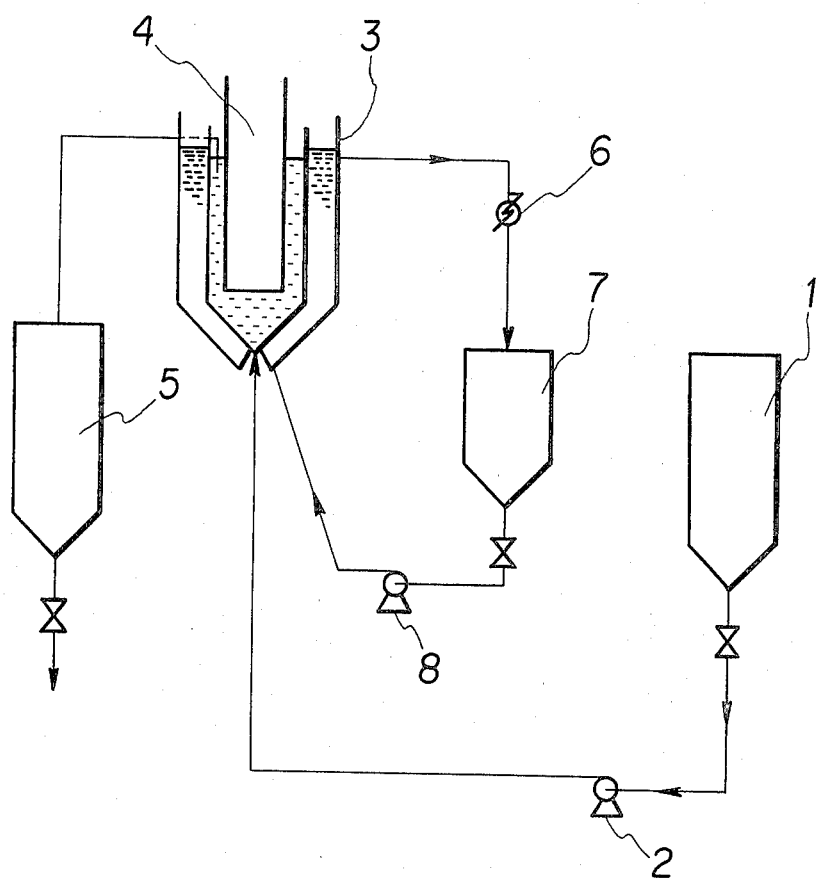

COLLAGEN FIBERS FOR USE IN MEDICAL TREATMENTS

BACKGROUND OF THE INVENTION

The present invention relates to novel collagen fibers for use in medical treatments and a process for preparing the same.

More in detail, the present invention relates to novel collagen fibers suitable for use in medical treatments prepared by dispersing refined collagen into an aqueous acidic solution and treating the thus obtained aqueous dispersion with a specified amount of energy by ultrasonic irradiation.

Collagen is a protein composed of corium, cartilage, bone, tendon, etc., and exists in the animal in a fibrilar or fiberlike state consisting of bound molecular collagens of about 2800 Å in molecular length and of about 15 Å in diameter which is called tropocollagen.

Since the cross-linking bonds generally proceeds between the molecules of collagen in the animal body with the aging of the animal, in the body of aged animal, the major part of collagen is "insoluble collagen".

The "insoluble collagen" in the present invention is collagen which is insoluble in an aqueous solution of an acid or a salt.

The collagen fibers obtained by mechanical fibrating or by chemical treatment of the insoluble collagen, having a property to be absorbed into the living body (bio-absorbability) and blood-coagulating property other than the low antigenic property have been expected as the blood-coagulant absorbable into the living body and the wound-treating material in the field of medical purpose.

The method of mechanical fibrating of collagen is a method in which insoluble collagen obtained from oxhide and the like is mechanically and severely crushed to be fibrated. However, even by such a mechanical means, the cross-linked bonds between the molecules of collagen are hardly broken, and accordingly, the collagen fibers obtained by mechanical fibrating are not excellent in bio-absorbability and in compatibility to living body.

In addition, since the quality of collagen fibers obtained by the mechanical means of fibrating depends largely on the kinds, the sex and the age of the animal from which collagen is derived, the collagen fibers having the uniform quality for use in medical treatments can not be always provided. For instance, the isoelectric point of insoluble collagen as the raw material of collagen fibers is the broad range of pH 5 to pH 8. The isoelectric point of insoluble collagen is one of the physical constants which indicate the degree of cross-linking between the molecules of collagen, and mainly depends on the kinds and the age of the animal. Accordingly, such a variation of the isoelectric point of insoluble collagen shows the difficulty of the production of the uniform quality of the insoluble collagen in the case where it is used for medical treatments.

As a method for solving the problem, the process for preparing "soluble collagen" fibers by selectively digesting and cutting the cross-linking bonds with protease without mechanically braking the molecules of collagen has been proposed (so-called the method for solubilizing by an enzyme).

The "soluble collagen" of the invention is collagen which may be soluble in an aqueous solution of an acid.

The method for solubilizing by an enzyme gives the collagen fibers having improved bio-absorbability and capability and the uniform quality, and then the method for solubilizing by an enzyme attain the initial object. However, the collagen fibers obtained by the method for solubilizing by an enzyme is not always satisfactory from the viewpoint of the poor blood-coagulating property of the product and of the high cost due to the use of expensive and unstable protease and the inability to re-use the protease.

In addition, according to the method for solubilizing by an enzyme, it is almost impossible to completely remove the protease intermixed into the soluble collagen fibers or to lose an activity of the enzyme without thermally denaturing the solubilized collagen fibers.

Accordingly, it is considered questionable from the viewpoint of safety to apply the soluble collagen fibers obtained by the method for solubilization by an enzyme to living bodies in the medical purpose. Further, it is difficult to control the action of the enzyme in digestion and cutting of the cross-linking bonds of raw collagen, and the attempts to obtain the homogeneity of the product inevitably lead to bring collagen into molecular state. The time period between the addition of collagen into a blood specimen and the beginning of blood-coagulation has a relationship to the degree of cross-linking between the molecules of collagen, and it is said that the time period is very long in the case of adding molecular collagen into the blood specimen.

Consequently, the conventional methods for obtaining the solubilized collagen fibers are not always satisfactory from the view-points of industry, economy and quality.

The object of the present invention is to provide collagen fibers having excellent in the properties such as bio-absorbability and velocity of blood-coagulation for use in medical treatments.

Another object of the present invention is to provide a process for producing collagen fibers for use in medical treatments. The other object of the present invention is to provide a hemostatica comprising collagen fibers for use in medical treatments.

SUMMARY OF THE INVENTION

In the first aspect of the present invention, there is provided collagen fibers for use in medical treatments, having amino acid residues of 312 to 340 glycine residues, 119 to 138 proline residues, 94 to 100 hydroxyproline residues and 2.6 to 5.5 tyrosin residues per 100 total amino acid residues thereof, a denaturation temperature in a range of 31° to 40° C. and S-constant of 1.12 to 1.62.

In the second aspect of the present invention, there is provided a process for preparing the collagen fibers for use in medical treatments, comprising the steps of dispersing purified collagen into an aqueous acid solution of pH 2 to 4, said purified collagen not showing any absorption in the ultraviolet rays of a wave length region of 250 to 290 nm and containing less than 0.5% by weight of lipid component, and irradiating the thus prepared aqueous dispersion with supersonic waves of higher than 108 kcal/liter of said aqueous dispersion at a temperature of not more than 30° C.

In the third aspect of the present invention there is provided a hemostatica comprising collagen fibers for use in medical treatment, having amino acid residues of 312 to 340 glycine residues, 119 to 138 proline residues, 94 to 100 hydroxyproline residues and 2.6 to 5.5 tyrosin residues per 1000 total amino acid residues thereof, a denaturation temperature in a range of 31° to 40° C. and S-constant of 1.12 to 1.62.

BRIEF EXPLANATION OF DRAWING

The drawing is a schematic illustration of an apparatus according to the present invention for supersonic irradiation of the aqueous acidic dispersion of collagen.

DETAILED DESCRIPTION OF THE INVENTION

The present invention relates to collagen fibers for use in medical treatments, having amino acid residues of 312 to 340 glycine residues, 119 to 138 proline residues, 94 to 100 hydroxyproline residues and 2.6 to 5.5 tyrosin residues per 1000 total amino acid residues thereof, a denaturation temperature in a range of 31° to 40° C., and S-constant of 1.12 to 1.62, and a process for preparing the collagen fibers for use in medical treatments, comprising the steps of dispersing purified collagen into an aqueous acid solution of pH 2 to 4, said purified collagen not showing any absorption in the ultraviolet rays of a wave length region of 250 to 290 nm and containing less than 0.5% by weight of lipid component, and irradiating the thus prepared aqueous dispersion with supersonic waves of higher than 108 kcal/liter of said aqueous dispersion at a temperature of not higher than 30° C.

The present inventors have found that the specific soluble collagen fibers obtained by dispersing the "purified collagen" into an aqueous acid solution of pH of 2 to 4 and irradiating the aqueous dispersion with a ultrasonic wave of higher than 108 kcal/liter as the amount of energy supplied by the irradiation of ultrasonic waves can be safely used in medical treatments and are excellent in the properties such as bio-absorbability and velocity of blood-coagulation (the reciprocal of the time period between the addition of collagen into a blood specimen and the beginning of blood coagulation) and have completed the present invention.

The present invention relates to the collagen fibers for use in the medical treatments, having amino acids per 1000 total amino acid residues of:
312 to 340 glycine residues,
119 to 138 proline residues,
94 to 100 hydroxyproline residues and
2.6 to 5.5 tyrosine residues,
and showing the denaturation temperature in a range of 31° to 40° C. and S-constant of 1.12 to 1.62, and a process for preparing the collagen fibers.

The reason why the remarkable differences of properties are recognized between the collagen fibers for use in medical treatments according to the present invention and the solubilized collagen obtained by the enzyme-treatment has not yet been elucidated theoretically. However, the difference is presumed to be caused by the difference between the homogeneities of collagen fibers of the present invention and that by the enzyme-treatment and the difference between the method for cutting of cross-linking bonds at the terminal parts of molecules of collagen.

In addition, the difference of the amount of residues of tyrosine between the two collagen fibers seems to support the presumption that the cutting of cross-linking by enzyme-treatment occurs as a result of digestion on the telopeptide at the terminal part of collagen molecule, and on the other hand, the cutting according to the process of the present invention occurs physically.

Further, the process according to the present invention is physical in nature, and since enzymes, caustic soda and sodium sulfate are not used in this treatment, there are no fear for their residues in the product. Accordingly, the safety of the product of the present invention as the material for medical use can be easily secured without carrying out the procedures for purification to remove such oxygenous impurities. In addition, the product according to the present invention is excellent in reproducibility and easily standardizable.

The present invention will be explained more in detail as follows.

As the raw material for the soluble collagen fibers according to the present invention, not-denatured connective tissues of warm-blooded animals such as cattle, swine, sheep and the like, for instance, hides, tendons, intestines and bones are mentioned, and raw hides, refrigerated hides, salted or dried hides are preferred because of their high content of collagen.

The "purified collagen" mentioned in the present invention is the collagen showing no absorption in the ultraviolet spectrum of wave length region of 250 to 290 nm, and containing lipids less than 0.5% by weight. The purified collagen is obtained by removing impurities such as proteins other than collagen (such as albumin, globulin, etc.), lipids, etc. from crude collagen obtained by subjecting the raw material to the conventional pretreatments such as depilation, decalcification, etc. The absorption of ultraviolet rays in the wave length region of 250 to 290 nm is derived from the amino acid residues which is hardly contained in collagen itself, and accordingly, it is used as an index of the degree of removal of proteins other than collagen (such as albumin, globulin, etc.) from the product.

The purified collagen can be prepared from crude collagen by the publicly known method of extraction. Namely, by repeated immersion of crude collagen into aqueous saline solution, the removal of proteins other than collagen is effected, and lipids can be removed by extraction with a mixed solvent, for instance, acetone-ethanol or acetone-ethanol-water, etc. The component of crude collagen, which is soluble in aqueous neutral salt solution may be removed by extracting with a phosphoric acid buffer containing disodium hydrogen phosphate and potassium dihydrogen phosphate, and the component of crude collagen, which is soluble in acid may be removed by extracting with a citric acid buffer containing citric acid and potassium dihydrogen citrate or a phosphoric acid buffer containing citric acid and disodium hydrogen phosphate. The removal of the soluble components of collagen is carried out until the protein in the extract becomes scarcely detectable by the method of copper-Folin. In addition, pH and concentration of the buffer solutions or the composition of the mixed solvent may be suitably changed according to the components to be removed.

The conditions for extraction is not particularly specified, however, the extraction is usually carried out at a temperature lower than 5° C. for one to a few days. In addition, the order of extraction is not particularly specified, and generally the extraction may be carried out in the following order: The following is an instance of the steps of preparation of purified collagen from raw collagen:

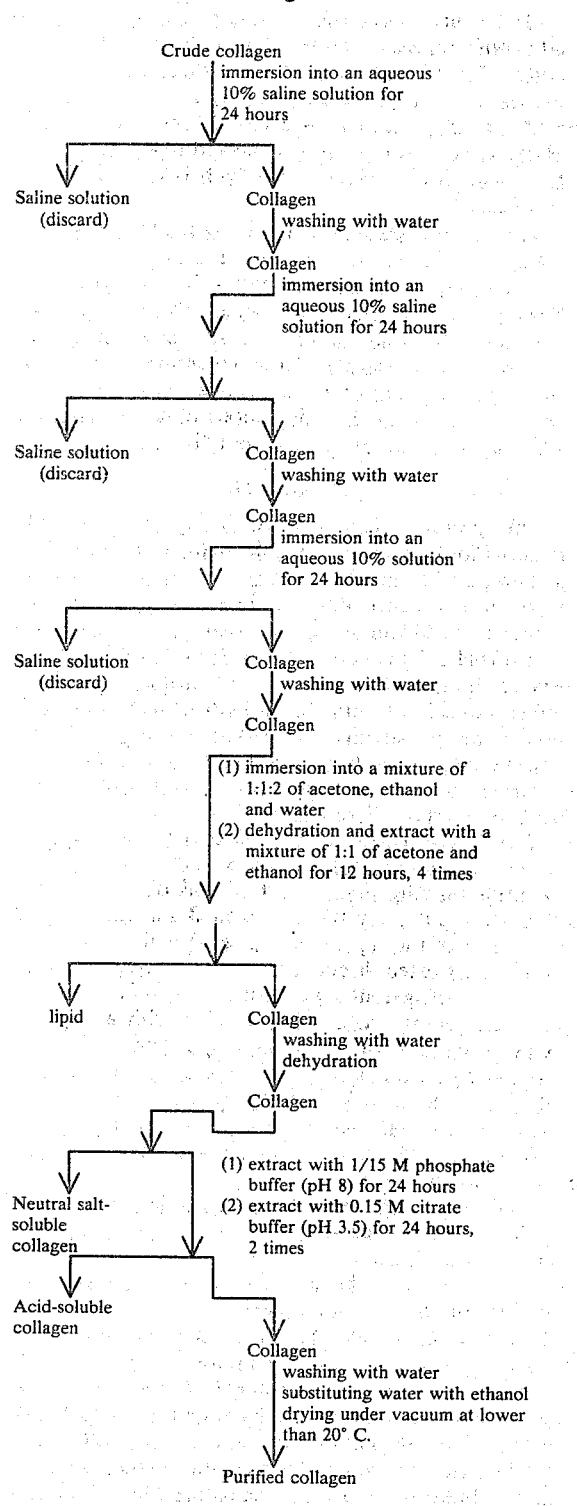

The collagen after passing through the purifying steps becomes homogeneous fibrous material consisting of insoluble collagen.

The pH of the aqueous acid solution for use in preparing an aqueous dispersion of collagen according to the present invention is in a range of 2 to 4. In the case of lower than pH 2, the once swollen and dispersed collagen fibers in the solution separates out from the dispersion and it is not favorable. On the other hand, in a range of pH 4 to 10, owing to the insufficient swelling of collagen fibers, an homogeneous state of dispersion is not available and collagen precipitates at the bottom of the vessel after leaving. In the case of subjecting the dispersion of such a state to ultrasonic waves treatment, collagen fibers begin to coagulate on the surface of the oscillator of ultrasonic waves and finally, all the collagen fibers adhere to the surface as a coagulated lump. In other words, the ultrasonic waves treatment in this range of pH 4–10 does not finely disperse the collagen fibers, and the appearance and the quality of the thus treated collagen are the same as those of the starting material.

Also in the region of pH of higher than 10, it is inconvenient because of the occurrence of denaturation of collagen fibers.

The content of collagen to be treated in the aqueous acid dispersion is 0.2 to 10% by weight, preferably 0.2 to 5% by weight. In the case of higher than 10% by weight, the viscosity of the dispersion is too high to be handled. On the other hand, in the case of lower than 0.2% by weight, there is a problem in economic efficiency.

The acid for use in making the aqueous acidic solution includes an inorganic acid such as hydrochloric acid, phosphoric acid and sulfuric acid, an organic acid such as acetic acid, butyric acid, citric acid, lactic acid, succinic acid and tartaric acid, and a mixture thereof.

The amount of energy supplied to the aqueous acidic dispersion by the irradiation of ultrasonic waves is $1.08 \times 10^2$ to $2.5 \times 10^3$ kcal/liter of the aqueous dispersion. The frequency of the ultrasonic waves for use in the present invention is not specified as far as it is in the range called ultrasonic (supersonic), but preferably is 17.5 to 24.5 kHz. The amount of energy by irradiation of ultrasonic waves depends on the S-constant of the collagen. Namely, the purified raw material, collagen, in the dispersion is fragmented or solubilized with the progress of irradiation of ultrasonic waves and finally brought into molecular state, and the change of the state of collagen during irradiation can be shown by the determination of the sedimentation velocity of the collagen in the dispersion. The S-constant of collagen fibers in the determination of sedimentation velocity of collagen fibers is the value concerning the state of basic unit of collagen and a factor having concerned the various physical properties of collagen. The S-constant of the collagen fibers according to the present invention is in a range of 1.12 to 1.62, measured by an apparatus, MOM 3170/b type tester (manufactured by MOM company, Hungary) at 20° C. and at a concentration of collagen of 2 mg/liter.

The irradiation of ultrasonic waves is carried out at a temperature of the aqueous acidic dispersion at which the denaturation of collagen is not caused, namely of not more than 30° C., preferably, not more than 20° C.

On carrying out the irradiation of ultrasonic waves under the conditions, the aqueous dispersion which is at first extremely dense viscous and opaque becomes less viscous and more translucent with the progress of solubilization of collagen by the irradiation, and finally transparent. The collagen fibers for use in medical treatments according to the present invention can be easily obtained from the thus prepared aqueous dispersion treated with the irradiation of ultrasonic waves by a series of known means of recovery such as neutralization, dialysis, freezing and drying.

The physical properties of the collagen fibers for use in medical treatments according to the present invention are as follows:

(1) amino acid composition of
   312 to 340 glycine residues,
   119 to 138 proline residues,
   94 to 100 hydroxyproline residues and
   2.6 to 5.5 tyrosine residues per 1000 total amino acid residues,
(2) temperature of denaturation of 31° to 40° C., and
(3) S-constant of 1.12 to 1.62.

These specific values of collagen fibers for use in medical treatments according to the present invention are close to those of tropocollagen.

By the irradiation of ultrasonic waves to the purified collagen as the raw material, cutting of cross linking bonds at the terminal part of the molecules of collagen occurs to produce the collagen fibers excellent in specificities suitable for use in medical treatments. The collagen fibers obtained by the treatment of the irradiation of ultrasonic waves show a striped pattern with a periodicity of 700 Å specific to collagen under an electronmicroscope. In addition, the fact that such collagen fibers have not been converted into gelatin is confirmed by the temperature of denaturation from the thus obtained collagen fibers to gelatin. Namely, as has been shown, the denaturation of the collagen fibers subjected to the irradiation ultrasonic waves occurs at a temperature in a range of 31° to 40° C., and the denaturation temperature of the unfibrating corium is 56° C. In addition, the denaturation temperature of the material obtained by mechanical fibrating of the unfibrating corium is 46° C., and the soluble collagen obtained by the digestion with the enzyme is 31° C.

The temperature of denaturation of collagen is determined by the scanning-type differential calorimeter (Model DSC-1 B, manufactured by Perkin-Elmer Company, U.S.A.) as follows:

After introducing 3 mg of air-dried collagen as a specimen in a pressure-resistant and closely sealable cell for DSC-determination and adding 10 microliters of water, the cell is sealed. After leaving the cell for 2 days at a room temperature to swell the specimen, the determination is begun at a temperature-raising rate of 2° C./min, and the apex of DSC-endothermal peak is taken as the "moist-denaturation temperature" of collagen (hereinafter abbreviated to as the denaturation temperature of collagen). In this case, as a control, the same type cell only containing 10 microliters of water is used. The two conditions, i.e. the amount of water introduced into the cell, and the temperature-raising rate have been respectively adopted by the following reasons: (1) the addition of more than 10 microliters of water did not affect the denaturation temperature as far as the temperature-raising rate is not changed, and (2) the dependency of the denaturation temperature on the temperature-raising rate disappears in the case where the temperature-raising rate is lower than 2° C./min.

The generally used methods for using the collagen fibers for use in medical treatments according to the present invention as the material for use in medical treatments are as follows:

(1) After subjecting the dispersion to the irradiation of ultrasonic waves, the dispersion is treated by neutralization or dialysis to recover the collagen fibers, and the thus recovered collagen fibers are dried to be lumps, and the lumps are disintegrated for the powdery product.

(2) The dispersion thus subjected to the irradiation of ultrasonic waves is directly freeze-dried to be porous bodies. The thus prepared dried bodies may be disintegrated to be the powdery product, or (3) The dispersion thus subjected to the irradiation of ultrasonic waves is further subjected to electro-deposition or casting to be a film, which is dried to be the film-like product.

The present invention will be concretely explained while referring to an example as follows.

However, the present invention is not restricted to Examples under mentioned. From the foregoing description, one skilled in the art can easily ascertain the essential characteristics of this invention, and without departing from the spirit and scope thereof, can make various changes and modifications of the invention to adapt it to various usages and conditions.

EXAMPLE

Fifty grams (dried weight of 12.5 g) of purified raw material for collagen (steerhide, native to North America) prepared from crude collagen by the pre-treatments were cut into cubes of about 5 mm in edge length, and immersed in 500 ml of aqueous hydrogen chloride solution of pH 2.5 for one night to be swollen. The acid-swollen fragments of collagen were dispersed by a juice mixer into 2.5 liters of aqueous hydrogen chloride solution of pH 3 and then the pH of the dispersion was adjusted to pH 3 with the addition of aqueous hydrogen chloride solution to obtain an aqueous dispersion of 0.5% by weight of collagen.

The thus obtained aqueous dispersion was subjected to the irradiation of ultrasonic waves in the apparatus shown in the drawing (1 is a feed tank of the dispersion; 2 is a feed pump for the dispersion; 3 is a reactor; 4 is an oscillator of the supersonic waves; 5 is the storage vessel of the treated dispersion; 6 is a cooler for a refrigerant; 7 is a refrigerant tank and 8 is a pump for circulating the refrigerant.), which is provided with a ultrasonic wave generator of 600 w in output and 19.5 kHz of frequency, while supplying the aqueous dispersion at the apex of the nozzle of the generator, cooling the vessel and keeping the temperature of the aqueous dispersion at 15° C. under the respective sets of the conditions shown in Table 1.

The thus respectively obtained acidic dispersions of collagen were freeze-dried to be the respective porous bodies of collagen.

Test of bio-absorbability on the thus obtained porous bodies of collagen and comparative collagens (untreated collagen and solubilized collagen by enzyme-treatment) was carried out as follows.

In this connection, the solubilized collagen by enzyme treatment was obtained by at first treating the raw material for collagen with an aqueous mixed solution of sodium hydroxide and sodium sulfate and then solubilizing the thus treated raw material at pH 9 by Pronase ®, a protein-hydrolysing enzyme prepared by Kaken Chem. Company, Japan.

Bio-absorbability Test

Each two pieces of porous bodies of the thus obtained collagen fibers, each weighing about 5 mg, were administered into the abdominal cavity of a male ICR-mouse of 6 to 7 weeks after birth and on the 4th day and the 7th day of administration, the mouse was sacrificed, and the state of the administered pieces of collagen fibers was observed and recorded.

The time taken for beginning blood-coagulation of the thus obtained porous bodies of collagen and the same control specimens as above was determined by adding each specimen of the collagen into platelet-rich human plasma and observing the coagulation of the blood by Platelet-aggregation-profiler (Model-PAP-3, manufactured by Bio-Data Company).

The results of the two series of tests are shown in Table 1.

As will be seen in Table 1, the collagen fibers according to the present invention is excellent in both blood-coagulating property and bio-absorbability as compared to the conventional collagen preparations, and accordingly, the collagen fibers according to the present invention can be used as a hemostatic.

TABLE 1

| Classification | No. of specimen | Heat of supersonic irradiation (kcal/liter) | S-constant | Temperature of denaturation (°C.) | Main amino acid composition | | | | Time period for blood-coagulation (sec) | Bio-absorbability |
|---|---|---|---|---|---|---|---|---|---|---|
| | | | | | glycine | proline | hydroxyroline | tyrosine | | |
| Present invention | 1 | 175 | 1.55 | 35 | 335 | 122 | 96 | 5.0 | 117.6 | partly remained on 4th day and all absorbed on 7th day |
| | 2 | 1290 | 1.17 | 34 | 338 | 120 | 97 | 4.9 | 120.0 | all absorbed on 4th day |
| | 3 | 2700 | 1.12 | 34 | 340 | 121 | 97 | 5.0 | 130.2 | all absorbed on 4th day |
| Comparative Ex. | 4 | 30 | 1.71 | 42 | 337 | 123 | 97 | 4.8 | 86.3 | all remained on 4th day and partly remained on 7th day |
| | 5 (1) | — | 1.82 | 56 | 340 | 122 | 96 | 4.9 | 32.4 | remained on 7th day |
| | 6 (2) | — | 1.10 | 31 | 337 | 122 | 96 | 0.5 | 146.4 | absorbed on 4th day |

Note:
(1) non-treated collagen (the raw material of the present invention) and
(2) solubilized collagen by enzyme-treatment.

What is claimed is:

1. Collagen fibers for use in medical treatments, having amino acid residues of 312 to 340 glycine residues, 119 to 138 proline residues, 94 to 100 hydroxyproline residues and 2.6 to 5.5 tyrosin residues per 1000 total amino acid residues thereof,
a denaturation temperature in a range of 31° to 40° C., and
S-constant of 1.12 to 1.62.

2. A process for preparing the collagen fibers for use in medical treatments, comprising the steps of dispersing purified collagen into an aqueous acid solution of pH 2 to 4, said purified collagen not showing any absorption in the ultraviolet rays of a wave length region of 250 to 290 nm and containing less than 0.5% by weight of lipid component, and irradiating the thus prepared aqueous dispersion with ultrasonic waves of higher than 108 kcal/liter of said aqueous dispersion at a temperature of not more than 30° C.

3. A process according to claim 2, wherein the content of said purified collagen in said aqueous dispersion is 0.2 to 10% by weight.

4. A process according to claim 2, wherein the irradiation of ultrasonic waves cause to change S-constant of said purified collagen.

5. Collagen fibers for use in medical treatments, having amino acid residues of 312 to 340 glycine residues, 119 to 138 proline residues, 94 to 100 hydroxyproline residues and 2.6 to 5.5 tyrosin residues per 1000 total amino acid residues thereof,
a denaturation temperature in a range of 31° to 40° C., and
S-constant of 1.12 to 1.62, obtained by a process comprising
dispersing purified collagen into an aqueous acid solution of pH 2 to 4, said purified collagen not showing any absorption in the ultraviolet rays of a wave length region of 250 to 290 nm and containing less than 0.5% by weight of lipid component, and
irradiating the thus prepared aqueous dispersion with ultrasonic waves of higher than 108 kcal/liter of said aqueous dispersion at a temperature of not more than 30° C.

6. A hemostatica comprising collagen fibers for use in medical treatment, having
amino acid residues of 312 to 340 glycine residues, 119 to 138 proline residues, 94 to 100 hydroxyproline residues and 2.6 to 5.5 tyrosin residues per 1000 total amino acid residues thereof,
a denaturation temperature in a range of 31° to 40° C., and
S-constant of 1.12 to 1.62.

* * * * *